United States Patent [19]

Renno et al.

[11] Patent Number: 5,565,486

[45] Date of Patent: Oct. 15, 1996

[54] SESQUITERPENES, THEIR PREPARATION AND THEIR USE AS INHIBITORS ACTING ON THE GABA-BENZODIAZEPINE RECEPTOR

[75] Inventors: Didier V. Renno; Gerard B. O'Beirne, both of Berkshire, United Kingdom; Brent R. Copp, Auckland, New Zealand

[73] Assignee: Xenova Limited, England

[21] Appl. No.: 464,737

[22] PCT Filed: Dec. 22, 1993

[86] PCT No.: PCT/GB93/02632

§ 371 Date: Aug. 29, 1995

§ 102(e) Date: Aug. 29, 1995

[87] PCT Pub. No.: WO94/14814

PCT Pub. Date: Jul. 7, 1994

[30] Foreign Application Priority Data

Dec. 22, 1992 [GB] United Kingdom ............... 9226724

[51] Int. Cl.$^6$ .......................... A61K 31/35; C07D 311/94
[52] U.S. Cl. ........................... 514/453; 549/383; 435/119
[58] Field of Search ............................. 549/383; 514/453

[56] References Cited

FOREIGN PATENT DOCUMENTS

| | | |
|---|---|---|
| 0395418 | 4/1990 | European Pat. Off. . |
| 0391503A3 | 10/1990 | European Pat. Off. . |
| 0405864A3 | 4/1991 | European Pat. Off. . |
| 0517484A3 | 2/1992 | European Pat. Off. . |
| WO91/16897 | 10/1991 | WIPO . |
| WO92/07853 | 10/1992 | WIPO . |

OTHER PUBLICATIONS

Patent Abstracts of Japan, vol. 12, No. 263 Jul. 1988 & JP, A, 63 048 284 (Yamanouchi Pharmaceutical Co. Ltd.) 29 Feb. 1988.

Advances in Drug Research vol. 14, 1985, pp. 165–322, Haefly W, et al 'Recent advances in the molecular pharmacology of benzodiazepine receptors and in the structure-activity relationships of their et al' see the whole document.

*Primary Examiner*—Johann Richter
*Assistant Examiner*—Laura L. Stockton
*Attorney, Agent, or Firm*—Nixon & Vanderhye

[57] ABSTRACT

Sesquiterpenes obtainable from the fungal strain *Acremonium strictum* XO6/15/458, and pharmaceutically and veterinarily acceptable salts thereof, are inhibitors of the binding of benzodiazepine to the GABA-benzodiazepine-Cl ionophore receptor complex. These compounds are prepared by (i) fermenting, in a source of carbon, nitrogen and inorganic salts, fungal strain XO6/15/458 (IMI 354451) or a mutant thereof which produces the sesquiterpenes, (ii) isolating the sesquiterpenes from the fermentation medium; and (iii) if desired, converting the sesquiterpene into a pharmaceutically or veterinarily acceptable salt.

8 Claims, No Drawings

SESQUITERPENES, THEIR PREPARATION AND THEIR USE AS INHIBITORS ACTING ON THE GABA-BENZODIAZEPINE RECEPTOR

This application is a 371 of PCT/GB93/02632 filed Dec. 22, 1993.

The present invention relates to novel benzodiazepine-receptor binding compounds. The invention further relates to the preparation of said compounds, to pharmaceutical and veterinary compositions containing them and to the microorganism from which they are obtained.

Benzodiazepine (Bz) is the conventional term used to describe the structurally related compounds with the basic benzo-1,4-diazepine structure (Haefely et al, Advances in Drug Res. 14 165–322 (1985)). Pharmacological screening of some of the early synthetic analogues of this novel ring system showed the benzodiazepines to have tranquillizing and anticonvulsant activity. Further investigation resulted in the launch of chlordiazepoxide (Librium) for therapeutic use in 1960.

Extensive electrophysiological and binding studies have established that the benzodiazepine mechanism of action involves allosteric modulation of the major inhibitory neurotransmitter, gamma-aminobutyric acid (GABA). More specifically, this effect results in the hyperpolarisation of neurons by increased Cl⁻ ion flux through the GABA-Bz-Cl⁻ ionophore receptor complex. This receptor complex has been designated subtype A, or $GABA_A$.

The majority of the currently prescribed benzodiazepines are agonists and act by potentiation of the GABA inhibitory effect. They therefore exert sedative, hypnotic, anticonvulsant and anxiolytic effects. Partial (low efficacy) agonists are also of interest since their use can reduce the undesirable effects of benzodiazepine therapy such as sedation, tolerance and addiction yet maintain their clinical effect. Inverse agonists having biological activity opposite to the classical benzodiazepine effects, i.e. convulsants, also have a postulated role in memory enhancement. Antagonists are devoid of biological activity but have applications in counteracting an excess of the above effects, i.e. overdose.

Structure activity relationships (SAR) for benzodiazepines have been fully characterised and the pharmacophore identified. Emphasis has therefore shifted to the identification of the endogenous receptor ligand, or novel structures as potential new drug candidates. Various chemical classes (e.g. benzazepines, β-carbolines, cyclopyrrolones, phenylquinolines, triazolopyridazines and imidazopyridines) have been shown to be active at this site. Zopiclone (a cyclopyrrolone derivative) and zolpidem (an imidizopyridine) have been launched as hypnotics.

It has now been found that fermentation of a nutrient medium with a strain of the fungus *Acremonium strictum* (Xenova organism X06/15/458, IMI 354451) produces novel compounds which inhibit the binding of benzodiazepine to the benzodiazepine receptor present on the GABA-Bz-Cl⁻ ionophore receptor complex. These compounds are sesquiterpenes which, together with their synthetic derivatives, form a novel class.

Accordingly the present invention provides a sesquiterpene of formula I:

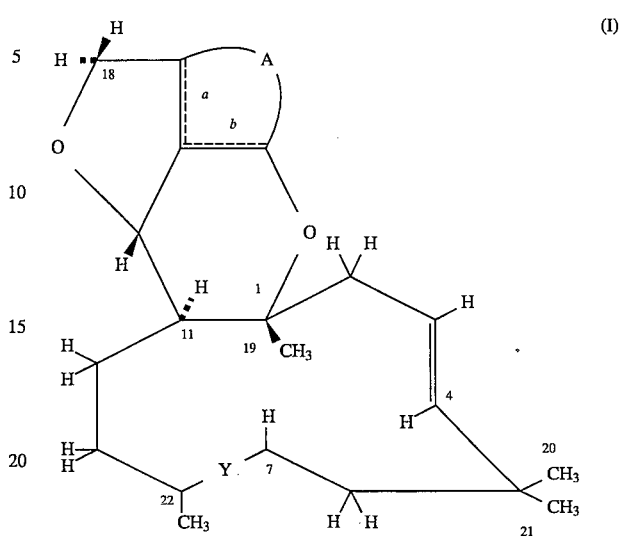

wherein each of

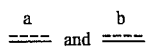

is a single bond or one is a single bond and the other is a double bond;

A, together with

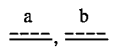

and the carbon atoms to which it is attached forms a ring selected from:

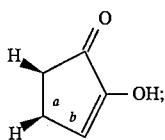

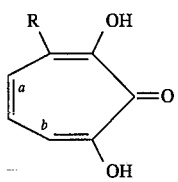

wherein R is H or OH;

wherein R is H or OH;

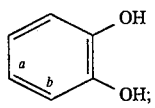

and

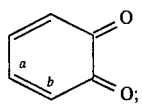

and Y is a double bond or, when A is a ring (a) as defined above Y is either a double bond or forms, together with the carbon atoms to which it is attached, an epoxide linkage;

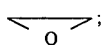;

and the pharmaceutically or veterinarily acceptable salts thereof.

In one embodiment, the sesquiterpene of formula I has the following structure II:

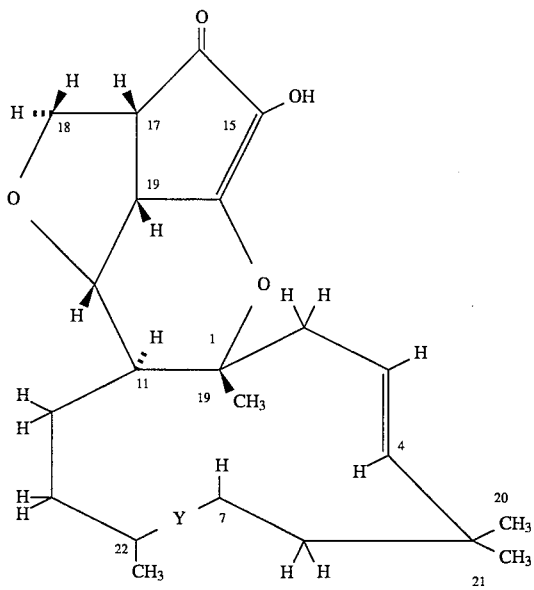

wherein —Y— is a double bond or forms, together with the carbon atoms to which it is attached, an epoxide linkage

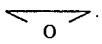.

In another embodiment the sesquiterpene of formula I has the following structure III:

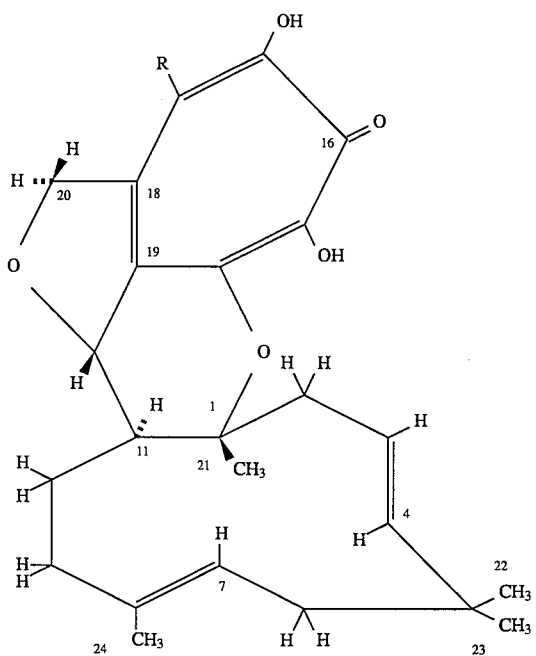

wherein R is H or OH.

In a further embodiment, the sesquiterpene of formula I is a compound of the following formula IV:

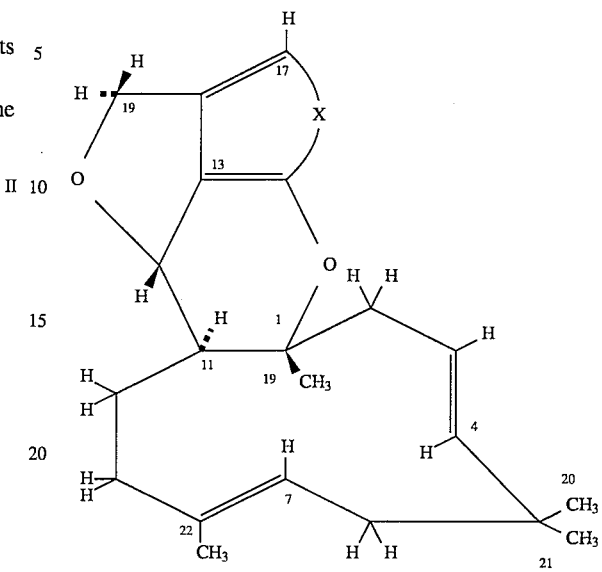

wherein X represents

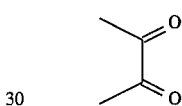

or

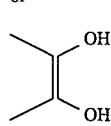

The sesquiterpene of formula II wherein Y is a double bond is hereinafter referred to as compound A. The sesquiterpene of formula II wherein Y forms, with the carbon atoms to which it is attached, an epoxide linkage is referred to as compound A'. The sesquiterpene of formula III wherein R is OH is referred to hereafter as compound B. The sesquiterpene of formula III wherein R is H is referred to as compound C. The sodium salt (15-ONa) of compound A is compound D. The sesquiterpene of formula IV wherein X represents

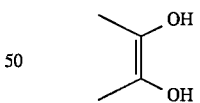

is compound E. The sesquiterpene of formula IV wherein X represents

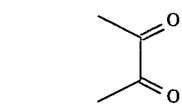

is compound F. Compound F is the 15,16 ortho quinone derivative of compound E. The term "the present compounds" when used hereafter refers collectively to all the sesquiterpenes of formula I and the pharmaceutically and veterinarily acceptable salts thereof.

The sesquiterpenes of formula I have been isolated from a microorganism which we have designated X06/15/458 and which has been identified as a strain of the fungus *Acremonium strictum* on the basis of the following morphological data:

When grown on 2% Malt Extract Agar for 10 days, colonies of strain X06/15/458 were 15–20 mm in diameter compared to 37–40 mm, sporulating copiously, pure white rather than varying in shades of off-white, comprised of dense, compact rather than loose mycelium; mostly velutinous and floccose only at the centre instead of tomentose at the centre, margin irregular, aerial not sharply delimited and immersed; conidiophores plectonematous to synnematous and superficial rather than submerged; mostly orthophialidic, rarely more complex, straight, gradually tapered, hyaline rather than chromophilous, up to 40–54 μm long×1.5 μm wide at the base compared with 20–40×1.5–2.0 μm. Conidia in slimey white masses cylindrical, 3.0–7.0×1.5 μm.

The organism exhibits the following differences from typical strains of *Acermonium strictum:* slower growth rate; pure white compact colonies; margin aerial, irregular and diffuse; conidiophores aerial and tending to synnematous; mean conidiophore length longer.

From the above described microscopic and gross morphological features, fungal isolate X06/15/458 is best classified as *Acremonium c.f. strictum* W. Gams as described in Gams, W. (1971) Cephalosporium-artige Schimmelpilze; Gustav Fischer publ.

The strain X06/15/458 was deposited under the Budapest treaty at the International Mycological Institute, Egham, Surrey, U.K. on 7th Oct. 1992 under accession number IMI 354451.

The above description is illustrative of a strain of *Acremonium strictum* which can be employed in the production of sesquiterpenes of the present invention. However, the present invention also embraces mutants of the above described microorganism. For example, those which are obtained by natural selection or those produced by mutating agents including ionising radiation such as ultraviolet irradiation, or chemical mutagens such as nitrosoguanidine or the like treatments, are also included within the ambit of this invention.

The present invention further provides a process for the preparation of the present compounds, which process comprises (i) fermenting, in a source of carbon, nitrogen and inorganic salts, fungal strain X06/15/458 (IMI 354451) or a mutant thereof which produces a sesquiterpene of formula I; (ii) isolating the said sesquiterpene from the fermentation medium; (iii) if desired, oxidising a sesquiterpene of formula I wherein A is ring (c) to a sesquiterpene of formula I wherein A is a ring (d) and/or (iv) if desired, converting the said sesquiterpene into a pharmaceutically or veterinarily acceptable salt thereof.

The sesquiterpenes of formula I are typically produced during the aerobic fermentation of an aqueous nutrient medium under conditions described hereinafter, with a producing strain of *Acremonium strictum* X06/15/458, or a producing mutant strain of X06/15/458. Aqueous media such as those used for the production of many antibiotic substances are suitable. Such nutrient media contain sources of carbon and nitrogen assimilable by the microorganism. If desired inorganic salts may be added, generally at low levels. In addition, the fermentation media may contain traces of metals necessary for the growth of the microorganisms, and production of the desired compounds. These are usually present in sufficient concentrations in the complex sources of carbon and nitrogen, which may be used as nutrient sources, but can, of course, be added separately to the medium if desired. A biologically pure culture of the fungal strain X06/15/458 or of a mutant which produces a sesquiterpene of formula I is a further aspect of the invention. Such cultures are substantially free from other microorganisms.

Assimilable sources of carbon, nitrogen and minerals may be provided by either simple or complex nutrients. Sources of carbon will generally include glucose, maltose, starch, glycerol, molasses, dextrin, lactose, sucrose, fructose, carboxylic acids, amino acids, glycerides, alcohols, alkanes and vegetable oils. Sources of carbon will generally comprise from 0.5 to 10% by weight of the fermentation medium.

Sources of nitrogen will generally include soya bean meal, corn steep liquors, distillers solubles, yeast extracts, cottonseed meal, peptones, ground nut meal, malt extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt, manganese, vanadium, chromium, calcium, copper, molybdenum, boron, phosphate, sulphate, chloride and carbonate ions.

An antifoam may be present to control excessive foaming and added at intervals as required.

The fermentation using *Acremonium strictum* X06/15/458 can be conducted at temperatures ranging from 20° C. to 35° C. preferably 24°–30° C. For optimal results, it is most convenient to conduct these fermentations at a temperature in the range 24°–26° C. The pH of the nutrient medium suitable for producing the compounds can vary from 5.0 to 8.5 with a preferred range of from 6.0 to 7.5.

Small scale fermentations are conveniently carried out by placing suitable quantities of nutrient medium in a flask by known sterile techniques, inoculating the flask with either spores or vegetative cellular growth of *Acremonium strictum,* loosely stoppering the flask with cotton wool, and permitting the fermentation to proceed in a constant room temperature of about 25° C. on a rotary shaker at from 95 to 300 rpm for 2 to 10 days.

For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Acremonium strictum.* The fermentation is allowed to continue for from 1 to 8 days while agitating and/or aerating the nutrient medium at a temperature in the range 24° C. to 30° C. The degree of aeration is dependent upon several factors such as the size of the fermenter and agitation speed. Generally the larger scale fermentations are agitated at about 95 to 500 rpm and aerations of about 0.1 to 1.0 vvm.

A sesquiterpene of formula I is found primarily in the mycelium on termination of the fermentation and may be recovered and purified. The separation and purification of the compound from the fermentation broth and its recovery can be achieved using solvent extraction followed by application of conventional chromatographic fractionations with various chromatographic techniques and solvent systems. The sesquiterpene can be obtained in substantially pure form.

The sesquiterpenes of formula I are soluble in organic solvents including ethyl acetate, methanol and acetone. This property may be used to recover them from the fermentation mycelium. Thus, the fermentation mycelium is suitably combined with approximately an equal volume of an organic solvent, for example acetone. The resulting crude extract may then be concentrated under reduced pressure to yield an aqueous suspension which is back extracted with an organic solvent to yield a crude organic extract. The total extract is filtered (or centrifuged) and the solvent concentrated under reduced pressure. The organic residue is then purified initially by chromatography, for example Sephadex LH-20 column chromatography with methanol as an eluent.

The desired product and some impurities are retained in the column, while many of the impurities (particularly the non-polar impurities) are not retained. The column is washed with a non-polar organic solvent such as hexane or toluene to remove further impurities, followed by sequential mixtures of dichloromethane or chloroform and another organic solvent such as methanol or ethyl acetate. The solvent is evaporated and the residue chromatographed further, for example by column chromatography, thin-layer chromatography, preparative-layer chromatography or high-performance liquid chromatography. In a preferred embodiment this further chromatographic step comprises repeated reversed phase C18 HPLC (25×10 cm, $CH_3CN:H_2O$ gradient).

Suitable adsorbents include silica gel and octadecyl bonded silica, whilst various solvents or combinations of solvents may be used as the eluent. Fractions of eluate are then examined by thin-layer, high-performance liquid chromatography or other conventional techniques to detect the presence of, and to isolate, the desired compound. The use of the foregoing techniques will afford purified compositions containing the desired sesquiterpene, the presence of which is determined by analysing the various chromatographic fractions for physico-chemical characteristics and/or for benzodiazepine-receptor complex binding activity.

The sesquiterpene of formula I wherein A is ring (c) (compound E) may be oxidised to its 15,16-orthoquinone derivative, which is a sesquiterpene of formula I wherein A is ring (d) (compound F). Compound F has the following structure:

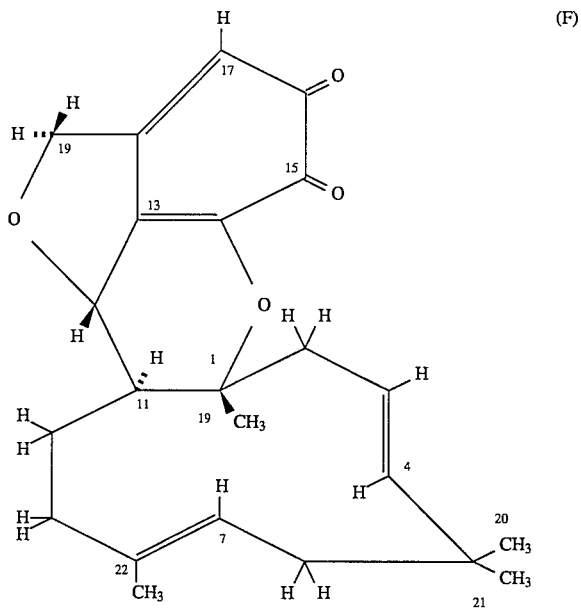

(F)

Oxidation may be achieved by allowing a solution of compound E to stand in air. Oxidation may alternatively be achieved, or aerial oxidation as described above may be accelerated, by adding an oxidising agent to a solution of compound E. A suitable example of an oxidising agent is sodium periodate ($NaIO_4$).

A sesquiterpene of formula I may be converted into a pharmaceutically or veterinarily acceptable salt.

Examples of suitable salts include those with alkali metals such as sodium and potassium, and ammonium salts. Compound D, the sodium salt of compound A, may for instance be prepared by treating compound A with sodium hydroxide in methanol.

The present compounds have activity in the treatment of disorders modulated by ligands for the benzodiazepine-receptor contained in the GABA-Bz-Cl⁻ ionophore receptor complex. A patient is treated according to the present invention by a method comprising administering to the patient a therapeutically effective amount of one of the present compounds. In this way the present compounds having agonist activity can be used to control conditions affected by the binding of benzodiazepine to the benzodiazepine receptor contained in the GABA-Bz-Cl⁻ ionophore receptor complex; they can therefore be used, for example, as anti-convulsants, anxiolytics, muscle relaxants and hypnotics. The condition of a human or animal may thus be improved.

The present compounds have shown activity in a benzodiazepine-receptor binding assay which uses a tritiated ligand specific for the receptor present on the purified GABA-Bz-Cl⁻ ionophore receptor complex. The details of the assay are set out in Example 5 which follows.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration for adult humans is 0,001 to 10 mg/kg, most commonly in the range of 0.01 to 5 mg/kg, body weight. Such a dosage may be given, for example, from 1 to 5 times daily orally or by bolus infusion, infusion over several hours and/or repeated administration.

The present compounds are formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form.

For example, the solid oral forms may contain, together with the active compound, diluents, such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dye-stuffs; sweeteners; wetting agents such as lecithin, polysorbates, laurylsulphates. Such preparations may be manufactured in known manner, for example by means of mixing, granulating, tabletting, sugar coating, or filmcoating processes.

Liquid dispersions for oral administration may be syrups, emulsions and suspensions. The syrups may contain as carrier, for example, saccharose or saccharose with glycerol and/or mannitol and/or sorbitol. In particular a syrup for diabetic patients can contain as carriers only products, for example sorbitol, which do not metabolise to glucose or which only metabolise a very small amount to glucose. The suspensions and the emulsions may contain as carrier, for example a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and if desired, a suitable amount of lidocaine hydrochloride. Solutions for intravenous injection or infusion may contain a carrier, for example, sterile water which is generally Water for Injection. Preferably, however, they may take the form of a sterile, aqueous, isotonic saline solution. Alternatively, the present compound may be encapsulated within liposomes.

The following examples illustrate the invention:

EXAMPLE 1

Culture of X06/15/458 in Liquid Media

Starting material of the strain X06/15/458 was generated by suspending a mature slant culture, grown on MEA (2% malt extract, 1.5% agar), in 5 ml 10% aqueous glycerol. 1 ml of this suspension, in a 1.5 ml cryovial, comprises starting material, which was retrieved from storage at −135° C. A preculture was produced by aseptically placing 0.5 ml starting material in 10 ml nutrient solution S (1.5% glycerol, 1.5% soya bean peptone, 1% D-glucose, 0.5% malt extract, 0.3% NaCl, 0.1% $CaCO_3$, 0.1% Tween 80, 0.1% Junlon PW110 (suppliers: Honeywell and Stein Ltd., Times House, Throwley Way, Sutton, Surrey, SM1 4AF) adjusted to pH6) in a test tube (25 mm×200 mm) shaken at 240 rpm for 4 days at 25° C.

An intermediate culture was then produced by aseptically transferring a preculture to 300 ml nutrient solution S in a 2l Erlenmeyer flask and incubating on a rotary shaker at 240 rpm for 3 days at 25° C.

A production culture was generated by aseptically transferring an intermediate culture to a 14l stirred fermenter containing 10l nutrient solution P (2.38% trehalose, 0.69% yeast extract, 0.1% carboxymethyl-cellulose, 0.1% Tween 80, 0.98% MES, adjusted to pH6). The vessel was agitated at 340 rpm and aerated at 0.7 vvm. The pH was uncontrolled but remained in the range 6.0 to 7.0. During the course of the fermentation the fermenter was maintained at a constant temperature of 25° C. After 7 days the fermentation was stopped and the biomass harvested for extraction of the product.

Larger scale fermentations employing 75 liter fermenters were performed as follows. A 40 ml preculture was prepared as described earlier (four 25×200 mm test tubes) and transferred to 2 liters of nutrient solution S in a 3 liter fermenter. The vessel was agitated at 500 rpm and aerated at 0.25 vvm. The pH was uncontrolled and the temperature maintained at 25° C. After 4 days this intermediate culture was aseptically transferred to a 75 liter fermenter containing 50 liters of nutrient solution P. The 75 liter vessel was aerated at 0.5 vvm and agitated at 350 rpm to maintain a dissolved oxygen tension >70% throughout the course of the fermentation. The pH was uncontrolled but remained between 6.0 and 7.0 and the temperature was held constant at 25° C. After 7 days the fermentation was stopped and the biomass harvested.

EXAMPLE 2

Extraction and Purification of Compound A

A 14l fermentation broth was centrifuged and the mycelium (−344 g) extracted with acetone (3×5l). The extract was concentrated to dryness (8.0 g) and redissolved in pure methanol. Purification was achieved by reverse phase preparative HPLC using a Waters Delta-Pak C18 (100Å, 15 μm) column (ID 10.0 mm, length 25.0 cm) and a mobile phase gradient of 4 minutes (80% aqueous acetonitrile, 12 ml/min flow rate) ramping linearly to 20 minutes (100% acetonitrile, 12 ml/min flow rate). Wavelength monitoring was at 280 nm.

The peak collected at 17–18 minutes was subjected to further purification using the same column but with a mobile phase gradient of 15 minutes (40% aqueous acetonitrile, 12 ml/min flow rate) ramping linearly to 20 minutes (100% acetonitrile, 12 ml/min flow rate).

The peak collected between 9 and 10 minutes was the sesquiterpene of formula II wherein Y represents a double bond. The compound had the following physical characteristics:

Molecular Formula: $C_{22}H_{30}O_4$

Molecular Weight: 358

Solubility includes Methanol, acetone, ethyl acetate

UV: [$\lambda_{Max}$(nm) ($\epsilon$)]: 276.6 (4900) MeOH 207.6 (30000) MeOH-KOH 311.2 (4100)

Mass spec.: [m/z ( intensity (%)]: DEI 358 ($M^+$,100), 233 (55), 203 (15), 155 (20) DCI ($NH_3$) 359 ($MH^+$,100), 233 (10), 203 (20), 155 (20)

High resolution CI: 359.2270, $C_{22}H_{31}O_4$ requires 359.2214

IR (KBr): [vin $cm^{-1}$: 3395.2, 2930.2, 1730.4

$^1$H-NMR: [400 MHz, $CD_3OD$, δ (m, J, posn)]: 1.13 (3H, s, 3H-21), 1.14 (3H, s, 3H-20), 1.37 (1H, m, H-10a), 1.51 (3H, S, 3H-19), 1.58 (1H, bddd, 13.2, 10.1, 6.8, H-10a), 1.72 (3H, s, 3H-22), 1.85 (1H, bdd, 13.0, 4.5, H-6a), 2.08 (1H, bdd, 12.5, 7.1, H-9a), 2.22 (1H, bdd, 9.8, 5.2, H-11), 2.23 (1H, bdd, 11.6, 11.6, H-9b), 2.33 (1H, bdd, 12.7, 12.7, H-6b), 2.38 (1H, dd, 14.5, 9.9, H-2a), 2.70 (1H, bddd, 14.5, 2.2, 1.6, H-2b), 3.02 (1H, ddd, 7.8, 5.6, 1.5, H-17), 3.67 (1H, dd, 5.8, 5.8, H-13), 3.80 (1H, dd, 9.3, 7.9, H-18a), 3.83 (1H, bdd, 6.0, 6.0, H-12), 4.03 (1H, bdd, 9.3, 1.5, H-18b), 5.17 (1H, m, H-7), 5.24 (1H, dd, 15.9, 1.5, H-4), 5.32 (1H, ddd, 15.9, 10.0, 2.2, H-3).

$^{13}$C-NMR: [100 MHz, $CD_3OD$, δ (m, posn)]: 17.66 (q, C-22), 23.71 (q, C-19), 24.92 (q, C-20), 30.85 (q, C-21), 32.24 (t, C-10), 37.37 (t, C-9), 39.37 (s, C-5), 42.22 (d, C-13), 43.11 (t, C-6), 45.01 (d, C-11), 45.17 (t, C-2), 48.97 (d, C-17), 70.86 (t, C-18), 83.70 (d, C-12), 88.94 (s, C-1), 121.90 (d, C-3), 124.68 (a, C-7), 135.25 (s, C-15), 137.39 (s, C-8), 144.73 (d, C-4), 166.96 (s, C-14), 200.99 (s, C-16).

EXAMPLE 3

Extraction and Purification of Compound B

A 75l fermentation was centrifuged and the mycelia extracted with ethyl acetate (5×10l). This extract was concentrated to dryness and redissolved in methanol. Purification was achieved by reverse phase preparative HPLC using a Waters Delta-Pak C18 (100Å, 15 μm) column (ID 10.0 mm, length 25.0 cm) and a mobile phase of 5 minutes at 80% aqueous acetonitrile (10 ml/min flow rate). Wavelength monitoring was set at 280 nm. The compound which eluted between 23 and 25 minutes was compound B, the sesquiterpene of formula III wherein R is OH. The compound had the following physical characteristics:

Molecular Formula: $C_{24}H_{30}O_6$

Molecular Weight: 414

Solubility includes Methanol, ethyl acetate, chloroform, acetone

| UV: | [λ_Max (nm) (ε)]: | |
|---|---|---|
| | 200 | HPLC solvent (H$_2$O—CH$_3$CN) |
| | 268 | |
| | 368 | |
| | 277.0 (29500) | MeOH |
| | 353.5 (3900) | |
| | 289.8 (32100) | MeOH—KOH |
| | 344.4 (3800) | |
| | 271.6 (47000) | MeOH—TFA |
| | 324.8 (3400) | |

Mass spec.: [m/z (intensity (%))]: DEI 414 (M$^+$,100), 331 (45), 277 (20), 211 (50) DCI (NH$_3$) 415 (MH$^+$,100)

High resolution EI: 414.2059, C$_{24}$H$_{30}$O$_6$ requires 414.2034 211.0240, C$_9$H$_7$O$_6$ requires 211.0240

IR (KBr): [ν in cm$^{-1}$]: 3265, 2960, 2930, 2855, 1735, 1625

$^1$H-NMR: [400 MHz, CDCl$_3$, δ (m, J, posn)]: 1.4(t), 1.7 (dd), 1.75(dd), 2.05(dd), 2.16(d+dd), 2.3(t), 2.4(dd), 2.7(dt), 4.9(d+td), 5.05(d+d), 5.2(dd), 5.25(dd).

$^{13}$C-NMR [100 MHz, CDCl$_3$, δ (m, posn)]: 160.4, 150, 146.1, 144.2, 144, 142.1, 136, 126.9, 123.7, 123, 118.7, 86.9, 84.3, 72.3, 43.5, 41.4, 40.7, 38.2, 37.7, 29.4, 28.2, 24.2, 22.7, 17

EXAMPLE 4

Extraction and Purification of Compound C

A 75l fermentation was centrifuged and the mycelia extracted with ethyl acetate (5×10l). This extract was concentrated to dryness and redissolved in methanol. Purification was achieved by reverse phase preparative HPLC using a Waters Delta-Pak PrepPak 3000 cartridge (C18, 100Å, 15 μm, ID 47 mm, length 30.0 cm) and a mobile phase gradient of 0.5 minute at 80% aqueous acetonitrile (50 ml/min flow rate) ramping linearly to 30 minutes at 100% acetonitrile (50 ml/min flow rate). The compound which eluted between 18 and 19 minutes was compound C, the sesquiterpene of formula II wherein R is H. This peak was further purified by using the same column but with a mobile phase gradient of 5 minutes at 30% aqueous acetonitrile (50 ml/min flow rate) ramping linearly to 10 minutes at 15% aqueous acetonitrile (50 ml/min flow rate). This solvent composition was then held for 15 minutes at 15% aqueous acetonitrile (50 ml/min flow rate) and then ramped linearly over 5 minutes to 100% acetonitrile (50 ml/min flow rate). The peak of interest, (compound C) eluted between 22 and 24 minutes under this gradient. The compound had the following physical characteristics:

Molecular Formula: C$_{24}$H$_{30}$O$_5$

Molecular Weight: 398

Solubility includes Methanol, acetone, ethyl acetate

| UV: | [λ_Max(nm) (ε)]: | |
|---|---|---|
| | 270.6 (41700) | MeOH |
| | 338.4 (3800) | |
| | 209.3 (13300) | MeOH—KOH |
| | 282.3 (41400) | |
| | 326.4 (3200) | |
| | 342.8 (3900) | |
| | 390.0 (3000) | |
| | 271.2 (52200) | MeOH—TFA |
| | 316.6 (4300) | |

Mass spec.: [m/z (intensity (%))]: DEI 398 (M$^+$,100), 315 (90), 256 (100), 233 (95), 195 (40) DCI(NH$_3$) 399 (MH$^+$, 100), 222 (10), 205 (90), 195 (20), 172 (70)

High resolution EI 398.2093, C$_{24}$H$_{30}$O$_5$ requires 398.2085

IR (KBr): [ν in cm$^{-1}$]: 3400 (sh), 3200, 2928, 1750, 1600, 1380

$^1$H-NMR: [400 MHZ, C$_6$D$_6$, Referenced to 7.16 ppm, δ(m, J, posn)]: 0.75* (3H, s, 3H-23), 0.93* (3H, s, 3H-22), 1.01 (3H,s, 3H-21), 1.11 (1H, t, 11.7, H-10a), 1.40 (1H, bdd, 14.9, 7.6, H-10b), 1.45 (3H, bs, 3H-24), 1.63 (1H, dd, 13.0, 5.0, H-6a), 2.05 (1H, bt, 11.5, H-6b), 2.10 (1H, m, H-2a), 2.11 (1H, m, H-9a), 2.17 (1H, dd, 11.0, 3.8, H-11), 2.60 (1H, t, 12.1, H-9b), 2.74 (1H, bd, 14.5, H-2b), 4.37 (1H, dd, 12.9, 1.6, H-20a), 4.44 (1H, dd, 13.0, 3.2, H-20b), 4.59 (1H, bdt, 11.2, 3.0, H-12), 5.01 (1H, dd, 15.8, 1.5, H-4), 5.11 (1H, dd, 15.8, 2.8, H-3), 5.15 (1H, bdd, 10.0, 3.2, H-7), 6.57 (1H, s, H-18).

$^{13}$C-NMR: [100 MHz, C$_6$D$_6$, Referenced to 128.00 ppm, δ (m, posn)]: 17.20 (q, C-24), 22.82 (q,C-21), 24.21* (q, C-23), 28.61 (t, C-10), 29.55* (q, C-22), 38.28 (t, C-9), 38.33 (s, C5), 41.44 (d, C-11), 41.93 (t, C-6), 43.98 (t, C-2), 75.35 (t, C-20), 85.28 (d, C-12), 86.75 (s, C-1), 108.49 (d, C-18), 120.05 (d, C-3), 124.20 (d, C-7), 127.94 (s, C-13), 136.22 (s, C-8), 137.45 (s, C-19), 143.74 (d, C-4) 147.96 (s, C-14), 149.71 (s, C-15), 160.00 (s, C-17), 165.58 (s, C-16).

EXAMPLE 5

Extraction and Purification of Compound A'

The biomass of X06/15/458 was collected by filtration, extracted successively with acetone (25L) and the extract separated from the biomass by filtration. Acetone was removed by rotary evaporation and the remaining aqueous slurry freeze dried to a gum. The gum was dissolved in methanol (250 ml), filtered then evaporated (150 ml). The sample was chromatographed by reverse phase HPLC using a 47×100 mm C$_{18}$ (octadecylsilica) Delta-Pak cartridge with 15 micron packing. A flow rate of 100 ml/min was used with a gradient 80% water—20% acetonitrile to 20% water—80% acetonitrile over a period of 30 minutes. Compound A was detected at 278 nm. The active fraction was re-chromatographed using the same column and flow rate with a gradient 60% water—40% acetonitrile to 35% water—65% acetonitrile over 40 minutes. The active fraction was concentrated on a rotary evaporator to remove acetonitrile and then freeze dried to a solid (compound A, batch 1).

Further purification was carried out by normal phase chromatography using flash column (30 cm×1.4 cm) filled to a depth of 16 cm with silica gel (MERCK, 230–400 mesh, particle 0.040–0.063 mm) and eluted isocratically with 40% hexane—60% ethyl acetate—1% acetic acid. The volatile solvent was removed under reduced pressure to yield a colourless oil, removal of residual solvent by freeze drier afforded a white crystalline solid (compound A, batch 3).

The product was stored in a freezer for six weeks. Reverse phase HPLC of the solid after storage was carried out on the Prep 3000 using a 25×100 mm cartridge packed with C$_{18}$-Nova-Pak HR (6 micron). A flow rate of 20 ml/min was used with a gradient 70% water—30% acetonitrile to 100% acetonitrile over a period of 20 minutes. In addition to compound A a second more polar component was isolated and identified as the 7,8-epoxide of compound A, compound A'. An alternative method to separate compound A from its 7,8-epoxide was to use the Delta-Prep with a gradient 60% water—40% acetonitrile to 40% water—60% acetonitrile over a period of 20 minutes.

Identification of compound A' was made by comparison of the UV, MS and NMR data with the corresponding data obtained for compound A (see Example 2).

Compound A' has the following physical characteristics:

Molecular Formula: $C_{22}H_{30}O_5$

Molecular Weight: 374

Solubility: MeOH (good)

UV: [λMax (nm)]
278 (Methanol)

| Mass Spec: | Technique | m/z | intensity (%) |
|---|---|---|---|
| | CI MH$^+$ | 375 | 100 |
| | MNH$_4^+$ | 392 | 2 |
| | EI M$^+$ | 374 | |
| | | 219 | 20 |
| | | 153 | 40 |
| | | 43 | 100 |

I.R. (KBr): ν in cm$^{-1}$: 3383 br, 2959 br, 1624, 1387.

$^1$H-N.M.R.: δ/ppm in CD$_3$OD: 1.13(3H,s), 1.29(3H,s), 1.39(3H,s), 1.45(1H, m), 1.49(3H,dd), 1.53(2H,m), 1.82(1H,dd), 2.00(1H,m), 2.10(2H,m), 2.55(1H,m), 2.75(1H,m), 2.80(1H,m), 3.00(1H,m), 3.70(1H,dd), 3.75(1H,dd) 3.80(1H,dd), 5.55(2H,d).

$^{13}$C-N.M.R.: δ/ppm in CD$_3$OD: 200.7($C_{16}$), 165.9($C_{14}$), 143.4($C_4$), 135.0($C_{15}$), 122.6($C_3$), 87.6($C_1$), 82.6($C_{12}$), 70.7($C_{18}$), 63.7($C_8$), 62.3($C_7$), 47.6($C_{11}$), 44.9($C_2$), 42.1($C_{13}$), 41.4($C_6$), 36.6($C_5$), 36.5($C_9$), 31.2($C_2$), 27.4($C_{10}$), 24.7($C_{20}$), 23.1($C_{19}$), 17.6($C_{22}$), 48.6($C_{17}$) -obscured by solvent.

EXAMPLE 6

Extraction and Purification of Compound E

A 75L fermentation broth of X06/15/458 was centrifuged and the mycelia extracted with ethyl acetate (5×10L). This extract was concentrated to dryness and redissolved in pure methanol. Purification was achieved by reverse phase preparative HPLC using a Waters Delta-Pak PrepPak 3000 cartridge (C18, 100 Å, 15 μm, ID 47 mm, length 30.0 cm) and an isocratic mobile phase of 40% aqueous acetonitrile (50 mL/min flow rate) for 50 minutes, followed by an acetonitrile flush for 10 minutes. The compound which eluted between 44 and 48 minutes was the target compound E. Wavelength detection was set at 200 nm. This peak was further purified by reverse phase semi-preparative HPLC using a Waters Delta-Pak column (C18, 100 Å, 15 μm, ID 10.0 mm, length 25.0 cm) and an isocratic mobile phase of 55% aqueous acetonitrile (15 mL/min flow rate) for 28 minutes, followed by an acetonitrile flush for 10 minutes. The compound eluting between 23 and 28 minutes was the target compound E. Wavelength detection was set at 200 nm.

Compound E has the following physical characteristics:

Molecular Formula: $C_{23}H_{30}O_4$

Molecular Weight: 370

Solubility: methanol, ethyl acetate

| UV: | [λ$_{max}$ (nm)] | (ε) | solvent]: |
|---|---|---|---|
| | 213.4 | 24400 | MeOH |
| | 230.0$_{SH}$ | 7500 | |
| | 277.3 | 9200 | |
| | 215.6 | 6900 | MeOH—KOH |
| | 228.2$_{SH}$ | 5400 | |
| | 286.1 | 5200 | |

Mass spec.: [m/z (intensity (%)]:

EI: 370 (M$^+$, 2%), 167 (80), 166 (100)

DCI (NH$_3$): 371 (MH$^+$, 30%), 205 (100), 167 (100), 149 (40), 135 (25), 123 (40), 121 (30), 109 (40)

IR (KBr): [ν in cm$^{-1}$]: 3333.4, 2932.2, 2862.7, 1720.7, 1622.3, 1496.9, 1381.2, 1329.1, 1286.7, 1167.1

$^1$H-NMR: [400 MHz C$_6$D$_6$/CD$_3$OD (referenced to CD$_3$OD at 3.40 ppm), δ (m, J, posn)]: 0.86* (3H, s, 3H-22), 1.07*(3H, s, 3H-21), 1.26 (3H, s, 3H-20), 1.36 (1H, dd, 13.6, 11.3, H-10a), 1.62 (3H, bs, 3H-23), 1.68 (1H, m, H-10b), 1.75 (1H, m, H-6a), 2.09 (1H, dd, 9.8, 8.6, H-11), 2.21 (1H, t, 12.3, H-6b), 2.27 (1H, dd, 12.7, 7.1, H-9a), 2.34 (1H, dd, 14.5, 10.3, H-2a), 2.70 (1H, bt, 11.7, H-9b), 2.84 (1H, dt, 14.5, 2.1, H-2b), 4.81 (1H, dd, 11.4, 1.2, H-19a), 4.88 (1H, bddd, 10.2, 2.3, 1.5, H-12), 5.02 (1H, ddd, 11.3, 2.5, 0.9, H-19b), 5.19 (1H, dd, 15.9, 1.7, H-4), 5.24 (1H, bddd, 11.9, 4.5, 1.2, H-7), 5.33 (1H, ddd, 15.9, 10.3, 2.4, H-3), 6.64 (1H, bs, H-17).

$^{13}$C-NMR: [100 MHz, C$_6$D$_6$/CD$_3$OD (referenced to CD$_3$OD at 49.00 ppm), δ (m, posn)]: 17.8 (q, C-23), 22.20 (q, C-20), 24.11* (q, C-22), 29.56 (t, C-10), 30.32* (q, C-21), 38.33 (s, C-5), 38.55 (t, C-9), 42.12 (t, C-6), 43.72 (d, C-11), 43.89 (t, C-2), 73.50 (t, C-19), 83.12 (d, C-12), 86.05 (s, C-1), 101.43 (d, C-17), 119.23 (s, C-13), 121.10 (d, C-3), 123.84 (d, C-7), 131.08 (s, C-15), 131.08 (s, C-18), 136.89 (s, C-8), 140.31 (s, C-14), 143.02 (d, C-4), 147.54 (s, C-16). *, **: assignments may be interchanged.

EXAMPLE 7

Preparation and Identification of Compound F

A solution of compound E, described in Example 6, in methanol was submitted to aerial oxidation accelerated by the addition of excess NaIO$_4$.

Purification of the compound was achieved by reverse phase preparative HPLC using a Waters Delta-Pak column (C18, 100 Å, 15 μm, ID 10.0 mm, length 25.0 cm) with a stepped solvent gradient of 25% aqueous acetonitrile (12 mL/min) for 5 minutes, ramping to 80% aqueous acetonitrile (12 mL/min) at time 35 minutes. The compound eluting between 30 and 32 minutes was the target compound F. Wavelength detection was set at 200 nm.

Compound F has the following physical characteristics:

Molecular Formula: $C_{23}H_{28}O$

Molecular Weight: 368

Solubility: methanol

| UV: | [λ$_{max}$ (nm) | (ε) | solvent]: |
|---|---|---|---|
| | 204 | | CH$_3$CN:H$_2$O hplc solvent |
| | 300 | | |
| | 482 | | |

$^1$H-NMR: [400 MHz, CD$_3$OD (referenced to CD$_3$OD at 3.40 ppm), δ (m, J)]: 6.03 (1H, bs), 5.24 (1H, dd, J=1.8, 15.9), 5.07 (1H, bdd, J=3.4, 10.9), 5.00 (1H, ddd, J=2.5, 10.6, 15.9), 4.79 (1H, dd, J=1.2, 15.6), 4.65 (1H, dd, J=2.2, 15.5), 4.55 (1H, d, 9.7), 2.63 (1H, dt, J=2.1, 14.8), 2.44 (1H, dd, J=10.5, 14.7), 2.27 (2H, m), 2.11 (1H, dd, J=7.2, 12.9), 1.88 (1H, d, J=9.0), 1.77 (1H, m), 1.65 (3H, s), 1.50 (1H, bt, J=11.0), 1.27 (3H, s), 1.07 (3H, s), 1.04 (3H, s).

$^{13}$C-NMR: [100 MHz, CD$_3$OD (referenced to CD$_3$OD at 49.00 ppm), δ (m)]: 180.16 (s), 175.03 (s), 159.46 (s), 144.57 (d), 137.71 (s), 124.25 (d), 120.6 (d), 114.37 (d), 88.75 (s), 81.63 (d), 71.91 (t), 43.40 (t), 42.68 (t), 42.58 (t), 39.19 (s), 38.96 (t), 30.52 (q), 30.22 (t), 24.50 (q), 21.90 (q), 17.21 (q).

EXAMPLE 8

Testing of the Present Compounds in a Benzodiazepine-receptor Binding Assay

The receptor extract was a crude synaptosomal preparation isolated from ox cerebral cortex by the method of Lang et al (FEBS Lett., 104 149–153, 1979). Receptor binding was determined using a modification described by O'Beirne and Williams (Eur. J. Biochem, 175 413–421, 1988) of the method of Braestrup and Squires (PNAS 74 3805–3809, 1977). The receptor preparation was incubated in 50 mM Tris/Cl, pH 7.4, with compound A and [$^3$H]-flunitrazepam (agonist) at a final concentration of 1 nM. Bound radioligand was harvested on to glass fibre filters and measured by liquid scintillation counting. Non-specific binding was determined by displacement of ligand with Diazepam (1 μM).

Binding data were fitted to one or two site models by weighted non-linear regression analysis using the computer programs 'LIGAND' (Munson and Rodbard: Analytic Biochem 107 220–239, 1980) and 'EBDA' (McPherson-Computer Prog. in Biomed. 7 107–114, 1983).

The method described above was repeated using each of compounds B and C described in Examples 3 and 4 respectively, and also using compound D, which is the sodium salt of compound A.

IC$_{50}$ values were also determined for compounds A', E and F described in Examples 5 to 7 respectively.

The results obtained were as follows:

TABLE 1

| Inhibition of binding of a benzodiazepine to the benzodiazepine receptor by the present compounds | | | |
|---|---|---|---|
| Compound | Concentration | % Inhibition | IC$_{50}$ |
| A | 93 μM | 107 | 40 nM |
| | 28 | 106 | |
| | 9 | 99 | |
| | 3 | 93 | |
| | 930 nM | 92 | |
| | 280 | 80 | |
| | 93 | 65 | |
| | 28 | 44 | |
| | 9 | 35 | |
| | 3 | 11 | |
| B | 177 μM | 78 | 5 μM |
| | 53 | 92 | |
| | 18 | 82 | |
| | 5 | 69 | |
| | 2 | 53 | |
| | 530 nM | 42 | |
| | 177 | 36 | |
| | 53 | 21 | |
| | 18 | 21 | |
| C | 242 μM | 88 | 20 μM |
| | 80 | 77 | |
| | 24 | 54 | |
| | 8 | 35 | |
| | 2 | 12 | |
| | 800 nM | 9 | |

TABLE 1-continued

| Inhibition of binding of a benzodiazepine to the benzodiazepine receptor by the present compounds | | | |
|---|---|---|---|
| Compound | Concentration | % Inhibition | IC$_{50}$ |
| | 240 | −3 | |
| | 80 | 9 | |
| D | 100 μM | 92 | 10 nM |
| | 50 | 103 | |
| | 10 | 100 | |
| | 5 | 98 | |
| | 1 | 86 | |
| | 500 nM | 81 | |
| | 100 | 65 | |
| | 50 | 70 | |
| | 10 | 45 | |
| | 5 | 45 | |
| A' | 2.8 × 10$^{-5}$ M | 104 | 85 nM |
| | 9.3 × 10$^{-6}$ | 103 | |
| | 2.8 × 10$^{-6}$ | 85 | |
| | 9.3 × 10$^{-7}$ | 83 | |
| | 2.8 × 10$^{-7}$ | 79 | |
| | 9.3 × 10$^{-8}$ | 51 | |
| | 2.8 × 10$^{-8}$ | 32 | |
| | 9.3 × 10$^{-9}$ | 19 | |
| | 2.8 × 10$^{-9}$ | 8 | |
| E | 9.5 × 10$^{-5}$ M | 104 | 500 nM |
| | 4.8 × 10$^{-5}$ | 101 | |
| | 9.5 × 10$^{-6}$ | 93 | |
| | 4.8 × 10$^{-6}$ | 88 | |
| | 9.5 × 10$^{-7}$ | 65 | |
| | 4.8 × 10$^{-7}$ | 52 | |
| | 9.5 × 10$^{-8}$ | 42 | |
| | 4.8 × 10$^{-8}$ | 37 | |
| | 9.5 × 10$^{-9}$ | 27 | |
| | 4.8 × 10$^{-9}$ | 22 | |
| F | 2.7 × 10$^{-4}$ M | 94 | 3.0 μM |
| | 9.0 × 10$^{-5}$ | 89 | |
| | 2.7 × 10$^{-5}$ | 77 | |
| | 9.0 × 10$^{-6}$ | 65 | |
| | 2.7 × 10$^{-6}$ | 48 | |
| | 9.0 × 10$^{-7}$ | 41 | |
| | 2.7 × 10$^{-7}$ | 33 | |
| | 9.0 × 10$^{-8}$ | 27 | |
| | 2.7 × 10$^{-8}$ | 24 | |
| | 9.0 × 10$^{-9}$ | 15 | |

EXAMPLE 9

Pharmaceutical Composition

Tablets, each weight 0.15g and containing 25 mg of one of the present compounds can be manufactured as follows:

Composition for 10,000 tablets

Present compound (250 g)

lactose (800 g)

corn starch (415 g)

talc powder (30 g)

magnesium stearate (5 g)

The present compound, lactose and half the corn starch are mixed. The mixture is then forced through a sieve 0.5 mm mesh size. Corn starch (10 g) is suspended in warm water (90 ml). The resulting paste is granulated to a powder. The granulate is dried and comminuted on a sieve of 1.4 mm mesh size. The remaining quantity of starch, talc and magnesium stearate is added, carefully mixed and processed into tablets.

We claim:

1. A sesquiterpene of the formula I:

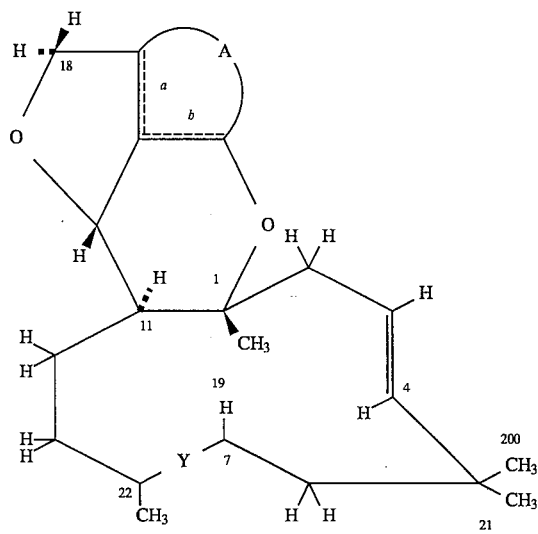

wherein each of $\underset{====}{a}$ and $\underset{====}{b}$ is a single bond or one is a single bond and the other is a double bond;

A, together with $\underset{====}{a}, \underset{====}{b}$ and the carbon atoms to which it is attached forms a ring selected from:

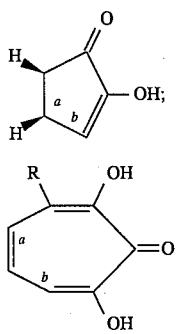

(a)

(b)

wherein R is H or OH;
wherein R is H or OH;

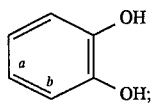

(c)

and

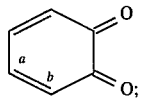

(d)

and Y is a double bond or, when A is a ring (a) as defined above Y is either a double bond or forms, together with the carbon atoms to which it is attached, an epoxide linkage $\overset{\frown}{O}$;

or a pharmaceutically or veterinarily acceptable salt thereof.

2. A sesquiterpene according to claim 1 of the formula II:

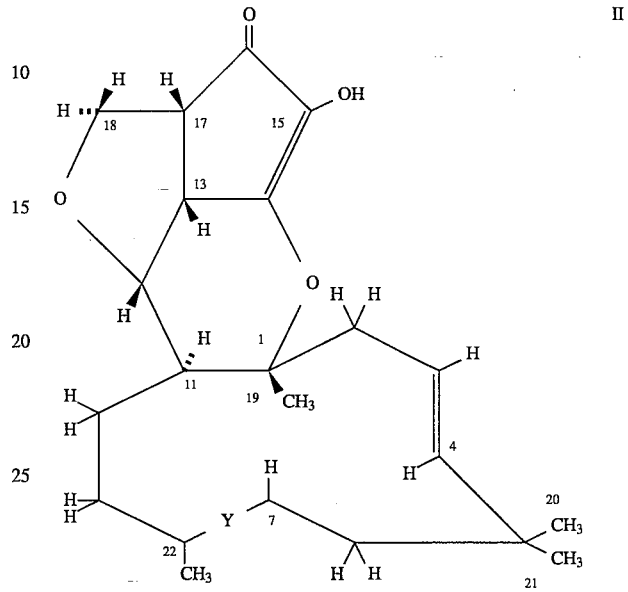

wherein —Y— is a double bond or forms, together with the carbon atoms to which it is attached, an epoxide linkage $\overset{\frown}{O}$;

or a pharmaceutically or veterinarily acceptable salt thereof.

3. A sesquiterpene according to claim 1 of the formula III:

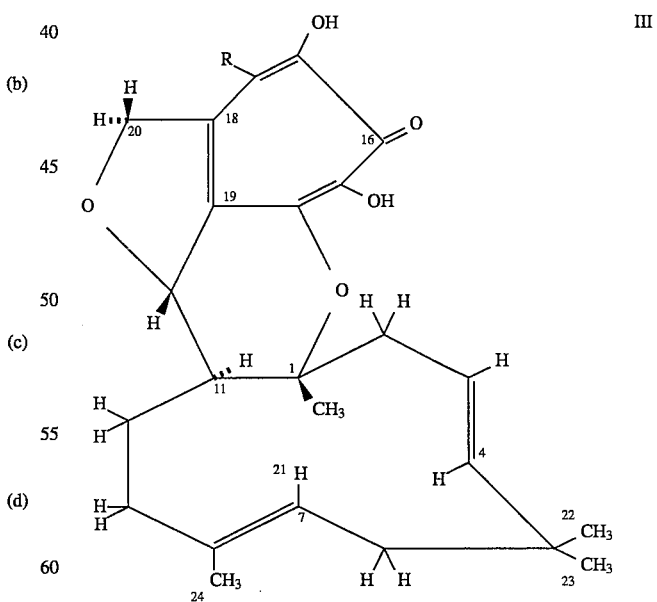

wherein R is H or OH, or a pharmaceutically or veterinarily acceptable salt thereof.

4. A sesquiterpene of the formula IV:

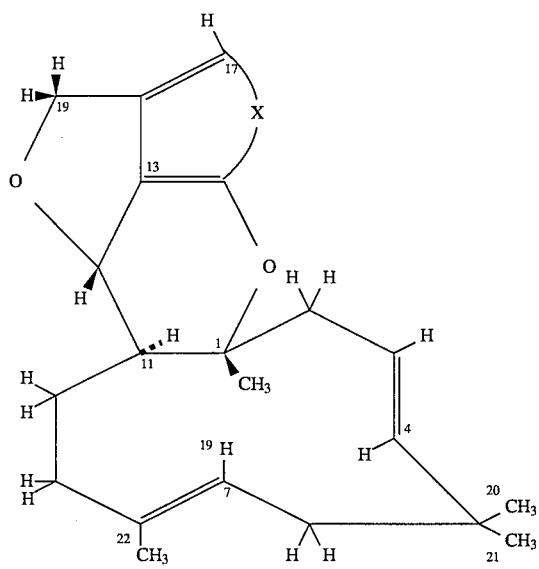

wherein X represents

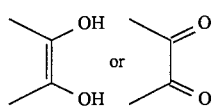

or a pharmaceutically or veterinarily acceptable salt thereof.

5. A process for the preparation of a compound as defined in claim 1 which process comprises (i) fermenting, in a source of carbon, nitrogen and inorganic salts, the strain of the fungus *Acremonium strictum* designated XO6/15/458 (IMI 354451) or a mutant thereof which produces a sesquiterpene of formula I; (ii) isolating the said sesquiterpene from the fermentation medium; (iii) if desired oxidising a sesquiterpene of formula I wherein A is ring (c) to a sesquiterpene of formula I wherein A is ring (d); and and/or (iv) if desired, converting the said sesquiterpene into a pharmaceutically or veterinarily acceptable salt thereof.

6. A pharmaceutical or veterinary composition comprising a pharmaceutically or veterinarily acceptable carrier or diluent and, as active ingredient, a compound as defined in claim 1.

7. A method for treating a disorder modulated by liganda for the benzodiazepine receptor in the gamma-aminobutyric acid-benzodiazepine-Cl ionophore receptor complex comprising administering to a person in need of same an effective amount of the compound of claim 1.

8. A method according to claim 7 wherein said patient requires an anti-convulsant, an anxiolytic, a muscle relaxant, a hypnotic, memory enhancer or drug overdose therapy.

* * * * *

UNITED STATES PATENT AND TRADEMARK OFFICE
CERTIFICATE OF CORRECTION

Page 1 of 4

PATENT NO. : 5,565,486
DATED : October 15, 1996
INVENTOR(S) : RENNO et al

It is certified that error appears in the above-identified patent and that said letters patent is hereby corrected as shown below:

In the Abstract line 2 correct the spelling of "pharmaceutically".
Column 2, line 51 delete "wherein R is H or OH;".
Column 5, line 18, correct the spelling of "*Acremonium*".
Column 17, delete the first formula and insert the following;
Column 17, line 49, delete "wherein R is H or OH;"
Column 18, claim 2, delete the formula and insert the following:

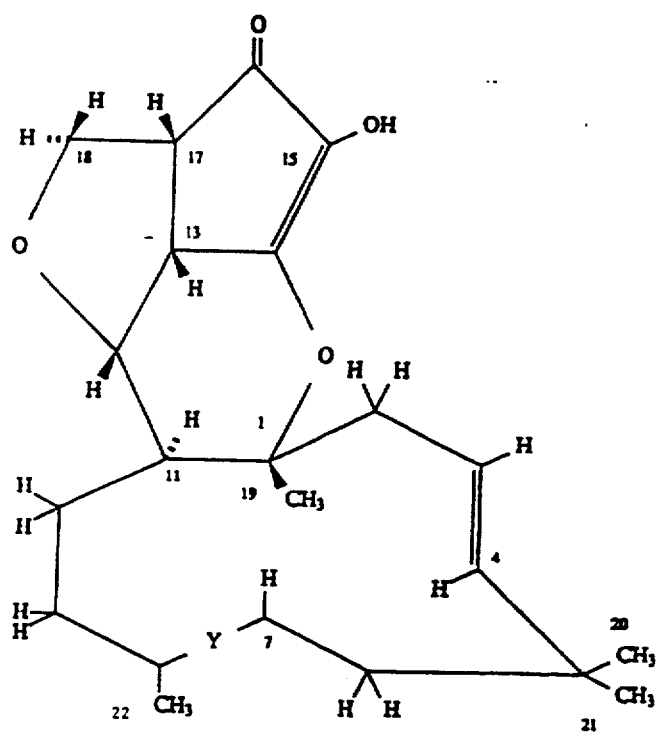

UNITED STATES PATENT AND TRADEMARK OFFICE
CERTIFICATE OF CORRECTION

Page 2 of 4

PATENT NO. : 5,565,486
DATED : October 15, 1996
INVENTOR(S) : RENNO et al

It is certified that error appears in the above-identified patent and that said letters patent is hereby corrected as shown below:

Column 18, claim 3, delete the formula and insert the following formula:

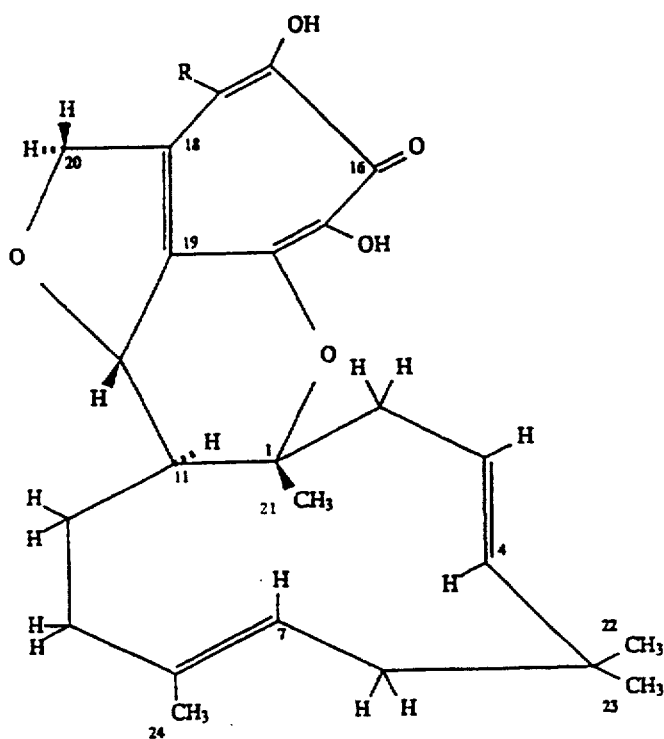

UNITED STATES PATENT AND TRADEMARK OFFICE
CERTIFICATE OF CORRECTION

PATENT NO. : 5,565,486
DATED : October 15, 1996
INVENTOR(S) : RENNO et al

Page 3 of 4

It is certified that error appears in the above-identified patent and that said letters patent is hereby corrected as shown below:

Column 19, claim 4, delete the first formula and insert the following:

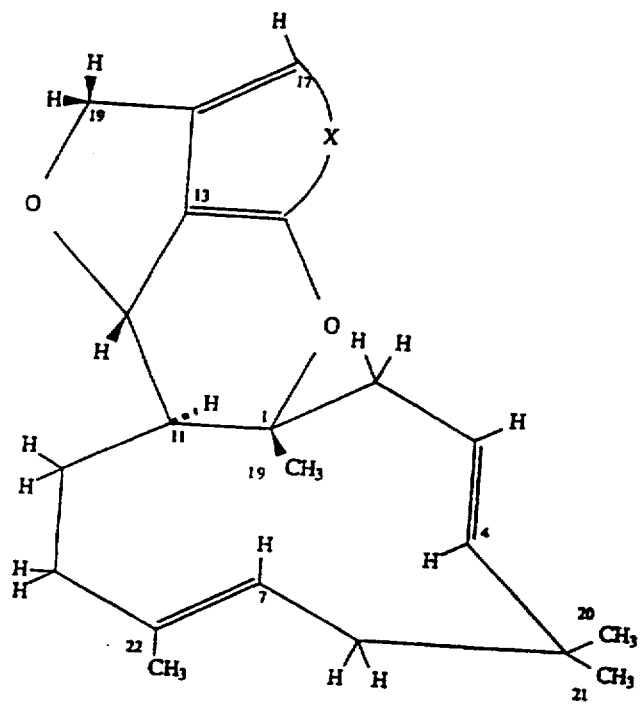

UNITED STATES PATENT AND TRADEMARK OFFICE
CERTIFICATE OF CORRECTION

PATENT NO. : 5,545,486

DATED : October 15, 1996

INVENTOR(S) : Renno et al

It is certified that error appears in the above-identified patent and that said Letters Patent is hereby corrected as shown below:

Column 20, line 7, correct the spelling of "ligands".

Signed and Sealed this

Twenty-fifth Day of March, 1997

Attest:

BRUCE LEHMAN

*Attesting Officer*        *Commissioner of Patents and Trademarks*